(12) United States Patent
Chen et al.

(10) Patent No.: US 8,895,805 B2
(45) Date of Patent: Nov. 25, 2014

(54) METHOD FOR MODIFYING INSECT RESISTANCE OF PLANTS BY UTILIZING RNAI TECHNIQUE

(75) Inventors: Xiaoya Chen, Shanghai (CN); Yingbo Mao, Shanghai (CN); Zhiping Lin, Shanghai (CN); Lingjian Wang, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 650 days.

(21) Appl. No.: 12/312,934

(22) PCT Filed: Dec. 4, 2007

(86) PCT No.: PCT/CN2007/071164
§ 371 (c)(1),
(2), (4) Date: Jun. 1, 2009

(87) PCT Pub. No.: WO2008/067759
PCT Pub. Date: Jun. 12, 2008

(65) Prior Publication Data
US 2010/0050294 A1  Feb. 25, 2010

(30) Foreign Application Priority Data

Dec. 4, 2006 (CN) .......................... 2006 1 0119029

(51) Int. Cl.
*C12N 15/82* (2006.01)
*C12N 15/87* (2006.01)
*A01H 1/00* (2006.01)

(52) U.S. Cl.
CPC ........ *C12N 15/8286* (2013.01); *C12N 15/8218* (2013.01)
USPC ........... 800/285; 800/279; 800/286; 800/288; 800/278; 536/24.5

(58) Field of Classification Search
None
See application file for complete search history.

(56) References Cited

U.S. PATENT DOCUMENTS

| | | | |
|---|---|---|---|
| 5,107,065 A | 4/1992 | Shewmaker et al. | |
| 5,231,020 A | 7/1993 | Jorgensen et al. | |
| 5,759,829 A | 6/1998 | Shewmaker et al. | |
| 6,326,193 B1 | 12/2001 | Liu et al. | |
| 6,506,559 B1 | 1/2003 | Fire et al. | |
| 7,999,148 B2 * | 8/2011 | Rathore et al. | 800/285 |
| 2002/0048814 A1 | 4/2002 | Oeller | |
| 2003/0018993 A1 | 1/2003 | Gutterson et al. | |
| 2003/0061626 A1 | 3/2003 | Plaetinck et al. | |
| 2003/0150017 A1 * | 8/2003 | Mesa et al. | 800/279 |
| 2003/0175965 A1 | 9/2003 | Lowe et al. | |
| 2004/0029283 A1 | 2/2004 | Fillatti | |
| 2005/0095199 A1 | 5/2005 | Whyard et al. | |
| 2005/0097637 A1 * | 5/2005 | Sainz et al. | 800/287 |
| 2006/0021087 A1 * | 1/2006 | Baum et al. | 800/279 |
| 2007/0259785 A1 * | 11/2007 | Heck et al. | 504/100 |

FOREIGN PATENT DOCUMENTS

| | | |
|---|---|---|
| WO | 94/01550 A1 | 1/1994 |
| WO | 98/05770 A2 | 2/1998 |
| WO | 99/49029 A1 | 9/1999 |
| WO | 99/53050 A1 | 10/1999 |
| WO | 01/37654 A | 5/2001 |
| WO | 01/37654 A2 | 5/2001 |
| WO | WO 01/37654 * | 5/2001 |
| WO | WO 2005/049841 A | 6/2005 |
| WO | 2005/110068 A2 | 11/2005 |
| WO | 2006/074400 A2 | 7/2006 |

OTHER PUBLICATIONS

EPO Communication dated Nov. 23, 2009, with Extended European Search Report and Written Opinion issued Nov. 23, 2009, by the European Patent Office in related European Application No. 07817354.9 (7 pages).

Database NCBI; Nucleotide; Sep. 26, 2006; XP002554085; Database accession no. D0986461 (2 pages).

Examiners Requisition (Final Office Action) issued Apr. 6, 2011, by the Canadian Intellectual Property Office in related Canadian Patent Application No. 2,671,425 (4 pages).

EPO Communication pursuant to Article 94(3) EPC (Office Action) issued Jul. 18, 2012, by the European Patent Office, in related European Patent Application No. 07 817 354.9 (6 pages).

Gordon, Karl H. J., et al., "RNAi for insect-proof plants"; Nature Biotechnology, vol. 25, No. 11, Nov. 2007; XP-002532186; pp. 1231-1232.

Examiner's Requisition (Office Action) issued Jul. 11, 2012, by the Canadian Intellectual Property Office (CIPO) in related Canadian Patent Application No. 2,671,425 (3 pages).

First Examination Report dated Feb. 11, 2013, issued by the Government of India Patent Office, in related Indian Patent Application No. 3877/CHENP/2009 (2 pages).

Official Action dated May 21, 2013, issued by the Mexico Patent Office, in related Mexican Patent Application No. MX/a/2009/005933, with partial English translation (5 pages).

(Continued)

*Primary Examiner* — Li Zheng
(74) *Attorney, Agent, or Firm* — Osha Liang LLP

(57) ABSTRACT

A method for improving insect resistance of plants, in which dsRNA of insect's gene is expressed in plants by using transgenic technique, and then the interfering RNAs are formed in the plants. The interfering RNAs then enter into insects' bodies after being ingested by the insect that eats the plant, and conduct RNA interference against the target gene, thereby expression of the target gene is suppressed by RNA interference. A new plant-mediated method for improving insect resistance by suppressing the growth of insects by RNA interference mechanism.

10 Claims, 5 Drawing Sheets

(56) References Cited

OTHER PUBLICATIONS

Mao, Ying-Bo, et al., "Silencing a cotton bollworm P450 monooxygenase gene by plant-mediated RNAi impairs larval tolerance of gossypol"; Nature Biotechnology, vol. 25, No. 11, Nov. 2007; p. 1307-1313.

Examiners Requisition (Office Action) dated May 14, 2014, issued by the Canadian Intellectual Property Office in corresponding Canadian Patent Application No. CA 2,671,425 (3 pages).

* cited by examiner

A

```
   1 GGCACGAGGC GAAGCTTCAC CATGATCACT TCATTGCTAC TAACGGCAGT TTTTGTGATA ATCTTCACAA TCTACCTCGT GTCCAAGAAA
  91 AAGTACCAAT ACTGGGAGAA AAGGAAAGTA CCACATTTAC CTCCGGTTCC TCTCCTGGGA AATTTTGGGA ACTTTATCCT GCAGAGGCAA
 181 TTTCTTGGCT ACACATTACA ACAAATATGT GGAAAGTTTC CCAACGTACC ATACGTGGGT GCCTATTTTG GCACAGAACC TGCCCTGATC
 271 GTCCAAGATC CTGAACACAT CAAGCTCGTC ATGACTAAGG ACTTCTACTT CTTCAGTTCC CGTGAGATAT CTGAATATGC CGACAGGGAA
 361 AGGTTTACTC AGAACCTCTT CTCCACTTCC GGAAACAAAT GGAAGGTGTT ACGTCAGAAC CTGACTCCAG TGTTTACCTC CGCGAAGATG
 451 AAGAACATGT TCCATTTGAT CGAAAAGTGT TCTCACGTGT TCGAAGATTT TCTCGATAAG GAACCCAAAA GCAACGAGGT CGAAATGAGG
 541 GCTCTTGTAG CGAGATACAC TATGGACTGC ATAGGAACCT GTGCATTTGG CGTTGAAACA AAAACCATGA ATGTGACGGA AAATAATCCG
 631 TTTACAGCAG TAGGTAACAG CATTTTCATG TTAAGCCGGG TCCAAGGATT TAAATTTGTT TTGCAGGGTA TCTACCCTTC ACTTTTCTAC
 721 TTGTTGGGAT TCAGAACTCT TCCACCAGAA GTTAATGCAT TCTTCTCCAA TTTAATGACT GGAGTTTTTA AGGGACGCAA CTATACGCCC
 811 ACATCTCGGA ATGACTTTGT CGATTTCGTA TTGAAGTGGA AACAAAATAA AACTATGACA GGGGACAGTC TGACTAACAT GAAATATGAT
 901 TCACAGAAAA AAGTGACTTT AGAAGTCGAC GATGATCTCT TAGTGGCACA GTGCTTTATA TTTTTTGCTG CTGGATATGA AACTTCGGCC
 991 ACCACTTTGA GTTTTACTTT GTATGAGTTG GCGAAACACC CAGAAGCTCA GAAGAGAGCT ATAGCCGAGG TGGACGATTA TCTGCGGCGA
1081 CACAACAATG AGCTGAAGTA CGAGTGCCTT TCGGAGATGC CATTTGTAGA AGCGTGCTTT GATGAGACTC TTCGTAAATA TCCAGTTTTA
1171 AGTTTGTTAA CTCGCGAAGT GGTAGAGGAT TACACTTTCC CTTCGGGATT GAAGGTAGAG AAAGGTCTCC GTATATTCCT GCCTCTGTAT
1261 CACTTGCACC ATAACCCGGA GTTCTTCCCG GATCCGGAGG AGTATAGGCC TGAGCGGTTC CTGCCTGAGA ACAAGGATAA AATAAAGCCG
1351 TACACGTACA TGCCCTTCGG TGAAGGCCCG AGACTTTGTA TTGGAATGAG ATTCGCGAAA ATGCAAATGA CCGCTGGAAT AATAACTTTG
1441 CTGAAAAAAT ACCGTTTGGA ACTGGCTCCA GGGATGCCCC AGAATATTGA ATTTGAACCT AATTCTTTTG TCTCGCAAGT TGCCGGAGGA
1531 ATCAATCTGA AGATGATAAA AAGAGAAAGT TGGGAAGGAA GACTACTGAA GAACCTCGAA AAGGCATATT AAAAAATTTG ACGTTCAGTT
1621 ATATAATCTT GTATGACTAA TCATAATTAC GCTTTATGTC TGGACTATCA TCACGTAGCA CTTATCACGC GATAGCAAAT TATAAATAGC
1711 AAATGTTGTG ATTGATTACA TGATTGATTT TTTTTTAAAT TAATATTTAG ATTGATTAGC TTTTAAAAAT TGTGTCAAAT ATGTTAAATT
1801 TGAAATGTCG TTATAAGTTG ACACTAAAGT AGCAGTAAAA GTTTTTTTTT TTAGCGCATT TAAATAAAAG CTTGTTTTTA AAGATTAAAA
1891 AAAAAAAAAA AAAA
```

B

```
MITSLLLTAVFVIIFTIYLVSKKKYQYWEKRKVPHLPPVPLLGNFGNFILQRQFLGYTLQQICGKFPNVPYVGAYFGTEP
ALIVQDPEHIKLVMTKDFYFFSSREISEYADRERFTQNLFSTSGNKWKVLRQNLTPVFTSAKMKNMFHLIEKCSHVFED
FLDKEAKSNEVEMRALVARYTMDCIGTCAFGVETKTMNVTENNPFTAVGNSIFMLSRVQGFKFVLRGIYPSLFYLLGF
RTLPPEVNAFFSNLMTGVFKGRNYTPTSRNDFVDFVLKWKQNKTMTGDSLTNMKYDSQKKVTLEVDDDLLVAQCFIF
FAAGYETSATTLSFTLYELAKHPEAQKRAIAEVDDYLRRHNNELKYECLSEMPFVEACFDETLRKYPVLSLLTREVVE
DYTFPSGLKVEKGLRIFLPLYHLHHNPEFFPDPEEYRPERFLPENKDKIKPYTYMPFGEGPRLCIGMRFAKMQMTAGIIT
LLKKYRLELAPGMPQNIEFEPNSFVSQVAGGINLKMIKRESWEGRLLKNLEKAY
```

C

```
  1 GGCACGAAGG GCGAATCACA GTGTGAGATA GAACAATTCA GAATGTCCTT AGACTTGTAT TACGCCCCTG GGTCGGCACC GTGCCGAGTG
 91 GTCCTGCTCG TAGCAGCAGC CCTCGACGTC CATTTTAATC CCCACATCTT AAACTTAAGA AATGGCGAAC ACCTCACACC AGAATTTTTG
181 AAGCTGAATC CCCAACACAC AGTGCCCACA CTAGTCGACG GCGACTTCTC TCTATGGGAG TCGAGAGCCA TCGGCAAATA CTTGGTGAAC
271 AAATATGGCG GCGAGAACAA CGACTTGTAT CCTAGTGATC CTAAAGCCAG GGCGATCGTC GACCAGAGAC TAGACTTCGA CTTGGGAACG
361 CTTTACCCAA GATTTGGAAA CTACATCTAT CCTCAAATCT TCGGTGGAGC GAAAGCAGAT GAGGCTCTGC TCAAGAAGCT GGAGGAAGCT
451 CTGCACTTCC TCAACACATT CCTCGAAGGT CAGAAGTACG CTGCGGGTGA CAAACTGACC TTGGCGACCG TCAGTCTCGT GGCGACTGTG
541 TCCACTATAG ACGCCGTCGA CATCAGCCTG AAGGAATATC CCAATGTTGA AAAGTGGTTC GAGCTGGTGA AAGCGACTGC CCCGGGATAC
631 CAGGAAGCAA ATGAAGCTGG CCTTAAAGCA TTCAGAGCTA TGGTAGCGCA GTTAAAAGCT AAAACTGAAT TGTAAGTGTA GCAGCATAAT
721 GCAATATTGT ATTTAGACGT ACAGAAGTAA GAGAGCATTT GCTCGCAGTA TAATAGTAAT ACTCGCATTT TGTAAGAAAT TGTCGTTAAG
811 TAAAAATATT TATATTTGAA AAAAAAAAAA
```

D

```
MSLDLYYAPGSAPCRVVLLVAAALDVHFNPHILNLRNGEHLTPEFLKLNPQHTVPTLVDGDFSLWESRAIGKYLVNKY
GGENNDLYPSDPKARAIVDQRLDFDLGTLYPRFGNYIYPQIFGGAKADEALLKKLEEALHFLNTFLEGQKYAAGDKLT
LADLSLVATVSTIDAVDISLKEYPNVEKWFELVKATAPGYQEANEAGLKAFRAMVAQLKAKTEL
```

FIG. 2

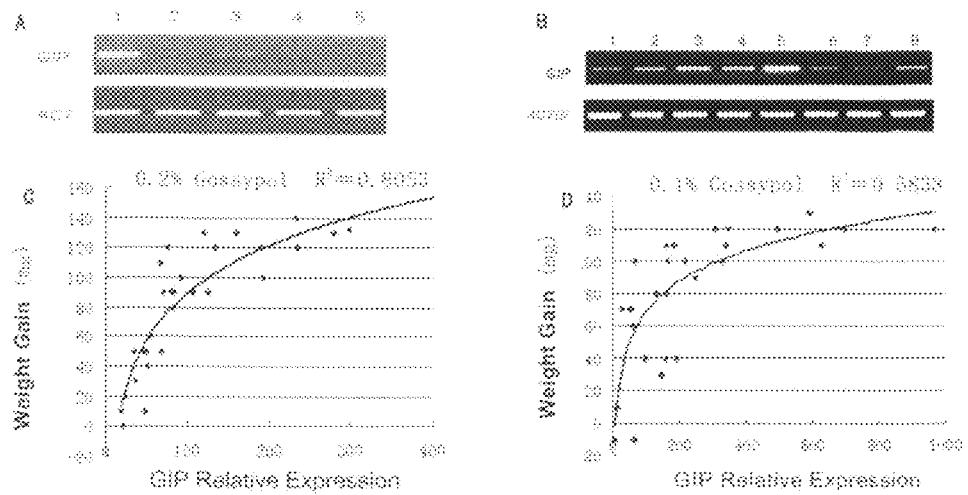
FIG. 3
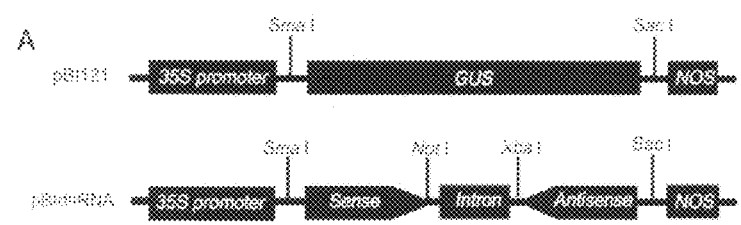
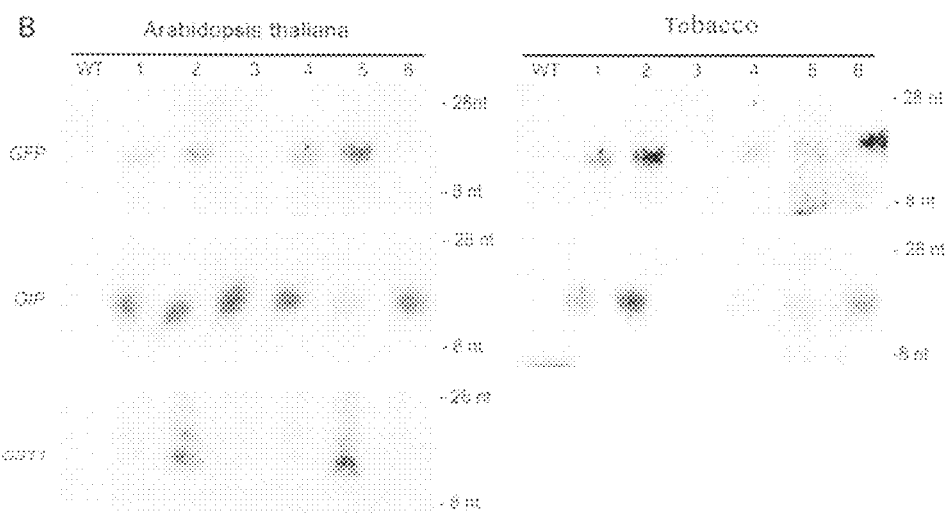
FIG. 4

METHOD FOR MODIFYING INSECT RESISTANCE OF PLANTS BY UTILIZING RNAI TECHNIQUE

TECHNICAL FIELD

The present invention relates to biotechnology and botany, particularly the present invention relates to new methods for modifying insect resistance.

BACKGROUND OF THE INVENTION

In agriculture, insect problem has always been an important factor to influence the agricultural output. Lots of human and material resources are put into inhibiting insect pest and improving the output.

Because of the increasing pesticide resistance and for the consideration of environmental protection and sustainable development, a new method for insect resistance is urgently needed. The invention of transgenic insect-resistant plant relieved this pressure, and has made great contribution to agriculture, such as transgenic insect-resistant soybean, Bt insect-resistant cotton, etc. However, there have been research reports that the resistance of various transgenic insect-resistant plants decreased with time, the insect pest that had been rarely seen previously occurred again.

Therefore, it is urgently needed to find a new method and develop a new transgenic insect-resistant plant to effectively and/or specifically resist the insect pest.

SUMMARY OF THE INVENTION

The present invention aims to provide methods for modifying insect resistance of plants by unitizing RNAi technique.

The first aspect of the invention relates to methods for improving insect resistance of plants, comprising the following steps:

Transfect constructs expressing insect gene dsRNAs into plant cells, tissues or organs, in which said constructs expressing insect gene dsRNAs are double-stranded, and their sense strands or antisense strands contain the following structure as Formula I:

$$Seq_{sense}\text{-}X\text{-}Seq_{antisense} \qquad \text{Formula I}$$

In which, $Seq_{sense}$ is a sense sequence or a fragment of an insect gene, in which said segment is at least 50 bp long;

$Seq_{antisense}$ is a sequence or a fragment complementary to $Seq_{sense}$, in which said segment is at least 50 bp long;

X is an intervening sequence between $Seq_{sense}$ and $Seq_{antisense}$, and said intervening sequence is complementary to neither $Seq_{sense}$ nor $Seq_{antisense}$.

In another preferred embodiment, said dsRNAs form interfering RNAs in plants.

In another preferred embodiment, said insect resistance is to resist insects that eat plants.

In another preferred embodiment, said constructs are on the expression vectors, and said expression vectors also contain promoters that can activate transcription in plants.

In another preferred embodiment, said insect genes are required for insect growth, or the genes that can influence insect growth or development under specific conditions (e.g. in the presence of or induced by pesticide, or phytoalexin).

In another preferred embodiment, said insect genes are expressed in insect stomach or intestines. Preferably, said insect genes are specifically or highly expressed in insect stomach or intestines.

In another preferred embodiment, said plants are selected from dicotyledon, monocotyledon or gymnosperm.

In another preferred embodiment, said plants are crop, flowers or forestry plants.

In another preferred embodiment, said plants include, but not limited to, cotton, tobacco, *arabidopsis thaliana*, rice, wheat, corn, sorghum and so on.

In another preferred embodiment, said insects are selected from those that eat plants.

In another preferred embodiment, said insects include, but are not limited to, cotton bollworm.

In another preferred embodiment, said intervening sequences are 80-300 bp long, preferably 100-250 bp.

In another preferred embodiment, said intervening sequences are introns.

The second aspect of the invention relates to the use of insect gene dsRNAs for making insect-resistant plants.

In another preferred embodiment, said gene is GIP gene of cotton bollworm.

In another preferred embodiment, said insect genes may be incorporated into a double-stranded construct, and their sense strands or antisense strands contain the following structure as Formula I:

$$Seq_{sense}\text{-}X\text{-}Seq_{antisense} \qquad \text{Formula I}$$

In which, $Seq_{sense}$ is a sense sequence or a fragment of an insect gene, in which said segment is at least 50 bp long;

$Seq_{antisense}$ is a sequence or a fragment complementary to $Seq_{sense}$, in which said segment is at least 50 bp long;

X is an intervening sequence between $Seq_{sense}$ and $Seq_{antisense}$, and said intervening sequence is complementary to neither $Seq_{sense}$ nor $Seq_{antisense}$.

In another preferred embodiment, after constructs expressing insect gene dsRNAs are transfected into plant cells, tissues or organs, the insect gene dsRNAs shown in Formula II are formed in the plant cells, tissues or organs,

Formula II

In which, $Seq_{sense}$, $Seq_{antisense}$ and X are defined as above,

∥ means there are hydrogen bonds formed between $Seq_{sense}$ and $Seq_{antisense}$.

The third aspect of the invention relates to plant cells, said plant cells containing constructs expressing insect gene dsRNAs, said constructs expressing insect gene dsRNAs are double-stranded, and their sense strands or antisense strands contain the following structure as Formula I:

$$Seq_{sense}\text{-}X\text{-}Seq_{antisense} \qquad \text{Formula I}$$

In which, $Seq_{sense}$ is a sense sequence or a fragment of insect gene, in which said segment is at least 50 bp long;

$Seq_{antisense}$ is a sequence or a fragment complementary to $Seq_{sense}$, in which said segment is at least 50 bp long;

X is an intervening sequence between $Seq_{sense}$ and $Seq_{antisense}$, and said intervening sequence is complementary to neither $Seq_{sense}$ nor $Seq_{antisense}$.

The fourth aspect of the invention relates to an isolated GIP protein, which is selected from the following group:

(a) a polypeptide with the amino acid sequence of SEQ ID NO: 2; or (b) a polypeptide with an amino acid sequence sharing at least 70% homology with that of SEQ ID NO: 2 and having the same functions as the polypeptide having the amino acid sequence of SEQ ID NO: 2.

The fifth aspect of the invention relates to an isolated polynucleotide, which is selected from the following group:
(a) a nucleotide sequence having the sequence of SEQ ID NO: 1; or
(b) a nucleotide sequence that can hybridize with SEQ ID NO: 1 under stringent hybridization conditions; or
(c) a nucleotide sequence sharing at least 70% identity with that of SEQ ID NO: 1; or
(d) a polynucleotide fragment having a sequence containing no less than 50 continuous nucleotides of SEQ ID NO: 1, and the fragment can silence the GIP gene; or
(e) a nucleotide sequence that is complementary to the sequences in (a), (b), (c) or (d).

The sixth aspect of the invention relates to use of the above-described polynucleotides for making preparations or plants that are capable of inhibiting insect growth.

In another preferred embodiment, said preparations or plants contain dsRNAs that can silence the GIP gene.

In another preferred embodiment, said dsRNAs contain the following structure as Formula I:

Seq$_1$-X-Seq$_2$     Formula I

In which,
Seq$_1$ is a sequence or a fragment of GIP gene, in which said fragment is at least 50 bp long;
Seq$_2$ is a nucleotide sequence or a fragment complementary to Seq$_1$, in which said fragment is at least 50 bp long;
X is an intervening sequence between Seq$_1$ and Seq$_2$, and said intervening sequence is complementary to neither Seq$_1$ nor Seq$_2$.

In another preferred embodiment, said insect is cotton bollworm.

The seventh aspect of the invention relates to methods for improving the stability of dsRNAs with not less than 50 nucleotides, characterized by: transfecting said dsRNAs into host cells, tissues or organs that are either without a dicer-like nuclease or with an inactive dicer-like nuclease.

In another preferred embodiment, said hosts are eukaryotes or prokaryotes.

The eighth aspect of the invention relates to use of GIP gene for making preparations or plants that are capable of inhibiting the growth of cotton bollworm.

In another preferred embodiment of the invention, said preparations for inhibiting cotton bollworm growth may contain interfering RNAs (such as siRNAs) for down regulating GIP gene expression.

In another preferred embodiment of the invention, said preparations may down regulate the expression of GIP gene in cotton bollworm.

In another preferred embodiment of the invention, said preparations may down regulate the expression of GIP gene in cotton bollworm by inhibiting the transcription of GIP gene.

In another preferred embodiment of the invention, said preparations may inhibit cotton bollworm growth by reducing resistance of cotton bollworm to gossypol.

In another preferred embodiment of the invention, said GIP gene contains the nucleotide sequence of SEQ ID NO: 1.

The stringent hybridization conditions in the invention refer to hybridization at 50° C. for 6-16 h, membrane-washing at 42° C. for 30 min, and the washing solution is 5×SSC with 50% formamide.

In view of the present description, other aspects of the invention can be readily appreciated by skilled persons in the art.

DESCRIPTION OF DRAWINGS

FIG. 2 shows the nucleotide sequences and the deduced protein sequences of GIP and GST1, in which, A: the nucleotide sequence of GIP (SEQ ID NO: 1); B: the protein sequence of GIP (SEQ ID NO: 2); C: the nucleotide sequence of GST1 (SEQ ID NO: 3); D: the protein sequence of GST1 (SEQ ID NO: 4). The sequences used for constructing dsRNA vectors in preferred embodiments of the invention are shaded. ATG: start codon; TAA: stop codon.

FIG. 3 shows that, in the presence of gossypol, the expression of GIP closely correlates with cotton bollworm growth.

FIG. 4A shows the construction of a dsRNA vector in accordance with one embodiment of the invention. FIG. 4A (top) shows a partial structure of PBI121 vector. FIG. 4A (bottom) shows a partial structure of PBIdsRNA constructed with PBI121 vector.

FIG. 4B shows the expression of transgenic tobacco and *arabidopsis thaliana* transfected with dsRNA with GIP, GFP or GST1 sequence by Northern blot assay.

DETAILED DESCRIPTION OF THE PREFERRED EMBODIMENT

After extensive and thorough research, the inventors unexpectedly found that interfering RNA (such as siRNA) of insect gene formed in plants can significantly inhibit the insect gene after ingestion. This inhibition is hardly or not at all affected by the insect digestive systems. Thus, the transgenic plants expressing interfering RNA of insect genes may be used to interfere or inhibit the expression of target genes in plant-eating insects by RNA interference after ingestion of the plants by such insects.

Thus, the inventors develop methods for inhibiting insect growth by using RNA interference mechanism using plants as vehicles. Namely, introducing constructs containing insect gene (or fragments) sequences into plants, the constructs in the plants can express dsRNAs of insect genes, which form interfering RNAs (such as siRNA). Insects eating such plants would ingest the interfering RNAs, which can inhibit gene expressions in the insects. As a result, insect growths can be inhibited.

Furthermore, the inventors also found, in cotton bollworm, that a gene plays a significant role in the detoxification of gossypol. The full-length gene is isolated from a cDNA library of *Helicovepa armigera*, and named GIP by the inventors. Further studies show that inhibition of GIP gene expression can significantly inhibit cotton bollworm growth and reduce the resistance of cotton bollworm to gossypol.

RNA Interference (RNAi)

The term "RNA interference" (RNAi) herein refers to certain double-stranded RNA that can block the expression of certain genes with high efficiency and specificity and facilitate mRNA degradation. Cells may show a specific phenotype resulting from specific genes being knocked down. This process is also referred to as RNA intervention.

The term "interfering RNA" refers to double-stranded RNA molecules, which can degrade target mRNA by hybridizing with the complementary sequences on the target mRNA. This process is referred to as RNA interference pathway.

Figure 1:
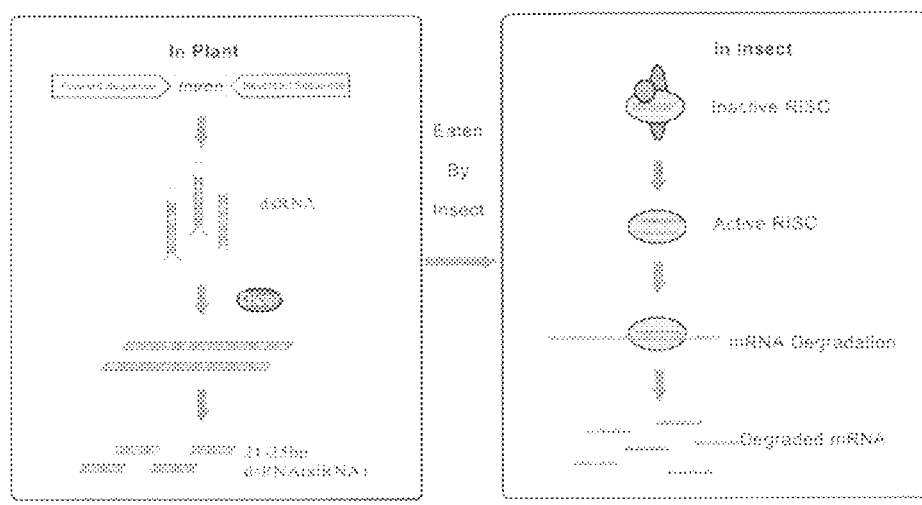
FIG. 1 shows a schematic illustrating the expression of dsRNAs derived from insect genes in plants, and subsequently inhibition of the expression of the related genes in insects that have eaten the plants.

In the invention, the basic principle of RNA interference is as follows: using plants as intermediary, allowing insects to ingest interfering RNAs (such as siRNA) that can interfere with insect gene expressions (such as GIP gene), leading to inhibition of insect growths. In particular, the principle is as follows: using gene transfection methods to express double-stranded RNAs (dsRNAs) derived from insect genes (full-length or part of genes) in plants to produce high levels of interfering RNAs in plants. After insects ingested such transgenic plants, large amounts of interfering RNAs are ingested. The interfering RNAs may in turn inhibit the expression of insect genes resulting in the inhibition of normal insect growths/developments, or even death, and, thus, achieving the goal of reducing plant damages by insects. As shown in FIG. 1, Dicer is RNAase III nuclease; RISC is RNA induced silencing complex, "intervening" means intervening sequence. Based on this principle, it is possible to effectively improve plant resistance to insects.

In accordance with preferred embodiments of the invention, an intron sequence is connected, at its two ends, to complementary sequences to form a "stem-loop" structure after transfection into cells. The "stem" can be processed by plants to become small RNAs of about 21-25 nt, which can effectively inhibit the expression of target genes.

Using RNA interference techniques to produce new transgenic plants with insect resistance may significantly impact agriculture development.

Methods for Improving Insect Resistance in Plants

Based on the principle of RNA interference, embodiments of the present invention provide methods for improving insect resistance in plants. A method in accordance with one embodiment of the invention includes: transfecting a construct expressing an insect gene dsRNA into plant cells, tissues or organs, wherein said construct expressing the insect gene dsRNA is double-stranded, the sense strand or antisense strand of which contains the following structure:

$$\text{Seq}_{sense}\text{-X-Seq}_{antisense} \quad \text{Formula I}$$

In which, $\text{Seq}_{sense}$ is a sense sequence of an insect gene or a fragment thereof, in which said fragment is at least 50 bp long;

$\text{Seq}_{antisense}$ is an antisense sequence of the same insect gene or a fragment thereof, in which said segment is at least 50 bp long;

X is an intervening sequence between $\text{Seq}_{sense}$ and $\text{Seq}_{antisense}$, and said intervening sequence is complementary to neither $\text{Seq}_{sense}$ nor $\text{Seq}_{antisense}$.

In accordance with a preferred embodiment, after the constructs expressing insect gene dsRNA are transfected into plant cells, tissues or organs, they are expressed in the plant cells, tissues or organs. The expressed insect gene dsRNA forms a structure shown in Formula II:

$$\text{Seq}_{sense} \overset{||}{\underset{}{\text{Seq}_{antisense}}} \diagup\hspace{-0.3em}\diagdown X \quad \text{Formula II}$$

In which, $\text{Seq}_{sense}$, $\text{Seq}_{antisense}$ and X are as defined above,

|| means hydrogen bonds formed between the $\text{Seq}_{sense}$ and $\text{Seq}_{antisense}$ double strand.

Embodiments of the invention are not limited to specific insect genes. To affect insects after their consumption of plants, the target insect genes are generally genes required for growth or those required for growth and development under specific conditions. Herein "genes required for insect growth" refer to those that play important roles in the growth, development, metabolism or reproduction (also referred to as "important genes for insect growth"). Low expression or lack of expression of these genes may lead to abnormality in the growth, development, metabolism or reproduction, or even death, in the insects. For use in the embodiment of the invention, the genes required for insect growth may be full-length genes or gene fragments. Specific conditions may be those in the presence of pesticide or phytoalexin. Because insects orally ingest interfering RNA, insect target genes are preferably those expressed to high levels in stomach or intestines. Selecting genes that are expressed in stomach or intestines can, to some extent, avoid problems associated with barriers or degradation, which may be encountered by using RNA interference to target genes in other tissues or organs in insects.

In accordance with preferred embodiments of the invention, insect genes may be selected from (but not limited to): P450 gene (GIP) or glutathione-S-transferase gene (GST1).

In accordance with preferred embodiments of the invention, the lengths of insect gene fragments are at least 50 bp long, e.g., 60 bp, 80 bp, 100 bp, 200 bp, 500 bp, 1000 bp, or full-length genes.

In accordance with embodiments of the invention, the intervening sequences are not limited to any specific lengths. Preferably, the intervening sequences and $\text{Seq}_{sense}$ and $\text{Seq}_{antisense}$ can form dsRNA of Formula II after being introduced into cells or body. Preferably, the intervening sequence is 80-300 bp long, more preferably 100-250 bp long.

In accordance with embodiments of the invention, constructs expressing insect gene dsRNA may be introduced into plant cells, tissues or organs. These plant cells, tissues or organs may be used to produce plants, in which insect gene dsRNA are expressed in the plants. The dsRNA forms interfering RNA (e.g. siRNA or other forms).

Generally, the above-mentioned constructs are based on expression vectors. The expression vectors generally contain promoters, replication origins and/or marker genes. An ordinary skilled person in the art would know how to construct expression vectors described in the invention. These methods include in vitro DNA recombination, DNA synthesis, in vivo recombination, and so on. Expression vectors preferably contain one or more selection maker genes for screening host cells having transformation phenotypes, such as resistance to kanamycin, gentamicin, hygromycin, or ampicillin.

Expression vectors harboring the above-described proper gene sequences and appropriate promoters or control sequences can be used to transform appropriate host cells. Host cells in accordance with one embodiment of the invention may be any that are suitable for harboring the expression vectors and for transferring the expression vectors to plant cells. Preferably, the host cell is an *agrobacterium*.

Although the insects described in the following examples are cotton bollworms, it should be understood that embodiments of the invention are not limited to any specific insects. Instead, insects in accordance with embodiments of the invention can be any insects that eat plants, such as lepidoptera insects.

Embodiments of the invention are not limited to any specific plants, as long as gene transfection can be performed with the plants, such as various crops, flowers, or forestry plants and so on. Plants can be (but not limited to) dicotyledon, monocotyledon or gymnosperm.

More specifically, plants include (but not limited to): cotton, tobacco, *arabidopsis thaliana*, rice, wheat, corn, sorghum, and so on.

GIP Gene

In accordance with one embodiment of the invention, the inventors use the GIP gene to produce insect resistant plants (transgenic plants).

GIP gene is expressed to high levels in the mesentera of cotton bollworms. The open reading frame of the gene contains 1578 bases (bp), which encodes 526 amino acid residues. FIG. 2A shows the DNA sequence of the gene (SEQ ID NO: 1) and FIG. 2B shows the protein sequence (SEQ ID NO: 2).

Immunohistochemistry and RT-PCR analysis show that GIP is highly expressed in the mesentera of cotton bollworms. GIP gene can be specifically induced by externally added gossypol compounds. In the presence of gossypol, the GIP expression levels show a positive correlation with the weight gains in cotton bollworms. Therefore, GIP is a critical gene for gossypol detoxification after cotton bollworms consume cotton plants containing gossypol. By introducing dsRNA vector containing GIP sequence into plants, GIP gene transcription in intestinal tissues is significantly inhibited, accompanied by an increased catalase activity, in the cotton bollworms that have ingested the transgenic plants. At the same time, larva growth is suppressed and gossypol resistance reduced due to down regulation of GIP gene in the mesentera of these cotton bollworms.

In accordance with one embodiment of the invention, the inventors use GIP gene to construct a dsRNA expression vector, introduce the vector into plants, produce transgenic plants, and feed cotton bollworm with the transgenic plants. The results show that the growths of the cotton bollworms are significantly inhibited after consumption of the transgenic plants.

Therefore, embodiments of the invention also include use of GIP gene for making preparations or plants that can inhibit cotton bollworm growth. The preparations may be used to down-regulate GIP gene expression in cotton bollworms. Preferably, the preparations are used to down regulate GIP gene expression in cotton bollworms by inhibiting GIP gene transcription. For example, the preparations for inhibiting cotton bollworms are those that contain interfering RNAs capable of down-regulating GIP gene expression.

GST1 Gene

In accordance with another embodiment of the invention, the inventors use glutathione-S-transferase gene (GST1) to produce transgenic plants to study whether RNA interference mechanism is working. FIGS. 2C and 2D show DNA sequence of GST1 gene (SEQ ID NO: 3) and protein sequence (SEQ ID NO: 4), respectively.

Figure 6:
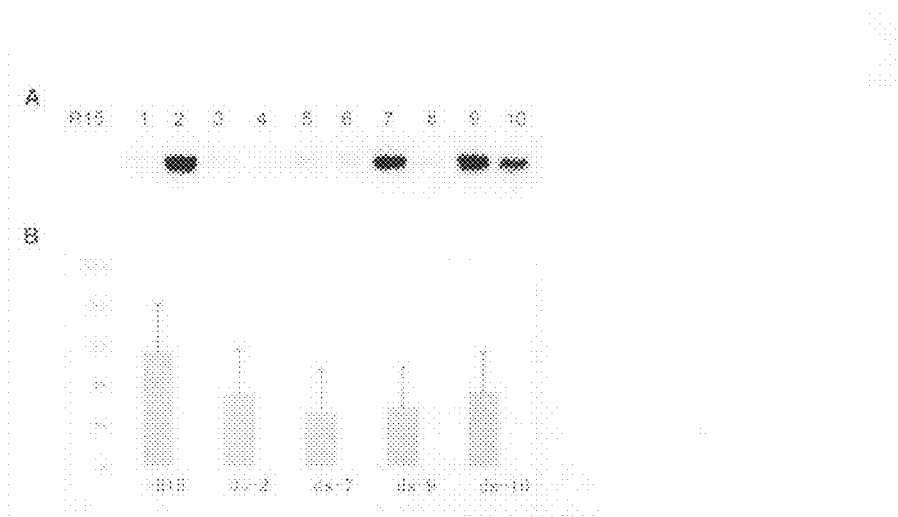
FIG. 6 shows the effects on cotton bollworm caused by the expression of dsRNA containing GIP sequence in cotton.

The inventors take GST1 gene as an example to construct a dsRNA expression vector and introduce it into plants. The results show that, after cotton bollworms consume the transgenic plants expressing dsRNA of cotton bollworm GST1 gene, the GST1 expression levels in mid gut of the cotton bollworms are down-regulated, and the enzymatic activity of GST is reduced in a total protein preparation from mid gut of the cotton bollworms (FIG. 6).

Large Fragment dsRNA can Effectively Mediate Gene Silencing

Figure 8:
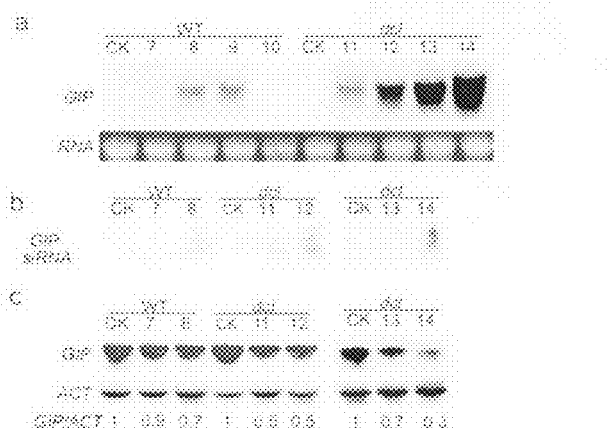
FIG. 8 shows inhibition of GIP expression in the mesenteron of cotton bollworms, which have ingested a plant containing dcl2 dcl3 dcl4 triple mutation constructs corresponding to the dsGIP sequence.

In accordance with yet another embodiment of the invention, the inventors skillfully use three *arabidopsis thaliana* mutants having mutations in dicer-like nuclease genes (i.e., dcl2 dcl3 dcl4 mutants) to study the effective forms of plant dsRNAs that induce insect gene silencing. *Arabidopsis thaliana* has 4 dicer-like nucleases (DCL), DCL1 is a relatively complex enzyme and can participate in the production of MicroRNAs and siRNAs. The other 3 DCL nucleases are mainly involved in the production of siRNAs. The inventors introduce a construct containing dsRNA of insect GIP gene into dcl2 dcl3 dcl4 mutant plants. The insect dsRNA is expressed in the plants. The majority of the dsRNAs maintain the original length and are not processed into siRNA. However, these dsRNAs can still silence the corresponding insect genes or have even better effects (FIG. 8).

The above results together suggest that the plant-mediated RNAi in insects may be a common mechanism, not limited to a specific gene. Therefore, using transgenic plants that express insect dsRNA to inhibit insects that eat plants may be used with various insect genes.

The invention has the following advantages:

(1) Previous RNA interfering methods are limited to inhibiting endogenous genes in the target organisms. In contrast, embodiments of the invention, for the first time, show that plants may be used as an intermediary to inhibit insect growth by RNA interference.

(2) This is the first demonstration that GIP is an important gene for detoxification of gossypol in cotton bollworms that consume cotton plants containing gossypol. Thus, insect growth may be inhibited by inhibiting GIP expression.

The present invention may be further illustrated in combination with the following examples. It should be appreciated that these examples are only for illustrating the invention and not for limiting the scope of the invention. Detailed experimental conditions not provided in these examples are generally conducted under conventional conditions, such as those described in Molecular Cloning: A laboratory manual, 3rd ed., Sambrook et al., Cold Spring Harbor Laboratory, 2001 or Plant Molecular Biology: A Laboratory Manual, Clark et al., Springer-Verlag, 1997, or under conditions suggested by the manufacturers.

Example 1

Characteristics of GIP Gene Expression

1. Expression of GIP Gene in Cotton Bollworm

In order to determine the expression of GIP gene in cotton bollworm, the inventors use a RT-PCR method to determine the expressions of GIP in different tissues. The method is as below: extracting mRNA from mesenteron of cotton bollworm, fat body, Malpighian tube, genitalia, and brain tissue, amplifying GIP gene by conventional RT-PCR method, testing the obtained amplified products for agarose gel electrophoresis, in which, the primers used in RT-PCR are shown in Table 1.

TABLE 1

| | | |
|---|---|---|
| GIP+ | 5'-GTGCTTTGATGAGACTCTTCG-3' | SEQ ID NO: 5 |
| GIP- | 5'-TACATTTGCTATTTATAATTTGC-3' | SEQ ID NO: 6 |

FIG. 3A shows RT-PCR products in gel electrophoresis. In the figure, lanes 1-5 represent the expressions of GIP gene in mesenteron, fat body, Malpighian tube, genitalia, and brain tissue respectively. ACTIN (ACT) serves as a positive control. It is clear that GIP gene is overexpressed in mesenteron of cotton bollworm.

2. Effects of Various Compounds on GIP Expression

The inventors use RT-PCR method to determine the effects of various compounds on GIP expression. The method is as below: one day after feeding the 5-day old cotton bollworm with the same growth vigor an artificial diet with or without 0.1% xanthotoxin, tannin, trans-cinnamic acid, gossypol, β-pinene, β-caryophyllene or α-pinene, mesenteron tissue of cotton bollworm are harvested, mRNA extracted, GIP gene amplified by conventional RT-PCR method, and the amplified products determined by agarose gel electrophoresis. The primers used in RT-PCR are the same as described in section "1".

The result is shown in FIG. 3B. In the figure, lanes 1-8 represent the expression of GIP gene in mesenteron of cotton bollworm fed with diet with or without 0.1% xanthotoxin, tannin, trans-cinnamic acid, gossypol, β-pinene, β-caryophyllene or α-pinene. It is clear that GIP expression is specifically induced by gossypol.

3. Effects of Various Concentration of Gossypol on GIP Gene Transcription

The inventors feed the 5-day old cotton bollworm with an artificial diet with 0.1% or 0.2% gossypol for 1 day. The levels of GIP gene transcription in mesenteron of each larva are determined by RT-PCT method (as described above).

The results are shown in FIG. 3C-D. It is clear that, in the presence of gossypol, the expression levels of GIP is closely correlated with cotton bollworm growth.

Example 2

Isolation of GIP Gene

Perform serial dilution of 1 µl *Helicovepa armigera* (about $10^6$ pfu) cDNA library (ZAP express), use the following specific primers for PCR, and determine the minimum working concentration of PCR:

```
GIP2+: 5'-GAAGATTTTCTCGATAAGGAAG-3'  (SEQ ID NO: 7)

GIP2-: 5'-ATATAAAGCACTGTGCCACTAAG-3' (SEQ ID NO: 8)
```

Submerge a 96-well plate in 70% ethanol for several hours and dry off. Expose under ultraviolet lamp for 15-30 min, add to each well with 200-300 µl LB (containing 10 mM $MgSO_4$/0.2% maltose). Mix well a library solution with certain dilution degree (1000×) and 400 µl XL1-Blue bacteria solution, shake culture at 37° C. for about 30 min, add 4 µl mixture into each well. Culture the plate at 37° C. overnight. After amplification, mix 5 µl bacteria solution from 8 wells of each row, total 12 rows for PCR. Perform PCR for each well in the rows with amplified strips. Select positive well for the next round of screening.

After 3 rounds of screening, plate phages on LB plate, select single phage plaques and transfer to 500 µl SM solution, shake, PCR verification to identify positive clones. Perform DNA sequencing on the positive clones, obtain full-length gene.

Example 3

Gene Isolation for the Construction of dsGIP, dsGST1

Using *Helicovepa armigera* cDNA library (ZAP express) as a template, the specific gene primer pairs:

A primer pair for obtaining GIP gene fragment:

```
GIPF:
5'-GAAGATTTTCTCGATAAGGAAG-3',    (SEQ ID NO: 7)
and

GIPR:
5'-ATATAAAGCACTGTGCCACTAAG-3';   (SEQ ID NO: 8)
and
```

A primer pair for obtaining GST1 gene (GenBank access no. EF033109) fragment:

```
GSTF:   5'-GACCTTGGCAGACCTCAG-3',    (SEQ ID NO: 9)
and

GSTR:   5'-CCAGCTCGAACCACTTTT-3';    (SEQ ID NO: 10)
```

After PCR amplification, GIP fragments and GST1 fragments may be obtained to construct dsGIP and dsGST1 expression vectors, respectively.

Example 4

Construction of Expression Vectors and Transfection

1. Construction of 35S::dsGFP, 35S::dsGIP, 35S::dsGST1 Expression Vectors

FIG. 4A shows pBIdsRNA, a dsRNA expression vector, includes a 35S promoter, a sense gene fragment (i.e. Sense), an intron of *arabidopsis thaliana* RTM gene (i.e. Intron) (about 120 bp), and an antisense gene segment (i.e. Antisense) and terminator of NOS. pBIdsRNA is constructed by replacing GUS fragment on pBI121 vector (shown in pBI121 of FIG. 4A) with a sequence containing Sense-Intron-Antisense.

The inventors first perform PCR amplification of intron (about 120 bp) of *arabidopsis thaliana* RTM gene (AT2G43730) with specific primers RTM+ and RTM-, which contain XbaI and NotI, with a high-fidelity DNA polymerase KOD. After double digestion of PCR products with XbaI and NotI restriction enzymes, the digested fragments are cloned into multiple cloning sites between XbaI and NotI of pBSK (purchased from Clontech company).

Perform PCR amplification using gene specific primers FGFP+ and FGFP-; FGIP+ and FGIP-; FGST1+ and FGST1-, which contain NotI and SacI restriction enzyme sites, a high-fidelity DNA polymerase, using GFP (from plasmid pCAMBIA 1302, this gene is not present in cotton bollworm) and GIP or GST1 obtained in Example 3 as templates, and clone the corresponding GFP, GIP and GST1 fragments. Perform double digestion on the cloned fragments with NotI and SacI, and insert the digested fragments between cloning sites (NotI/SacI) on pBSK vector, which harbor RTM intron.

At the same time, perform PCR amplification with specific gene primers RGFP+ and RGFP-; RGIP+ and RGIP-; RGSL+ and RGSL-, which contain SmaI and XbaI enzyme sites, with a high-fidelity DNA polymerase KOD, using GFP and GIP or GST1 obtained in Example 3 as templates, and clone the GFP, GIP, GST1 fragments between SmaI and XbaI of pBSK of the previously described sense GFP, GIP and GST1 fragments.

Perform double digestion on the pBSK/dsGFP, pBSK/ds-GIP, and pBSK/dsGSL vectors with SmaI and SacI. Perform double digestion on pBI121 (purchased from Clonetech company) with SmaI and SacI to remove GUS. Insert dsGFP, dsGIP, dsGSL fragments obtained from double digestion between SmaI and SacI to obtain recombinant expression vectors carrying with corresponding target fragments, i.e., 35S::dsGFP, 35S::dsGIP, 35S::dsGST1 expression vectors.

The primers used in the construction are shown in Table 2.

TABLE 2

| Designations | Sequences | SEQ ID NO: |
|---|---|---|
| RTM+ | 5'- CCCTCTAGAACGTTGTAAGTCTGATTTTTGAC -3' | 11 |
| RTM- | 5'- CCCGCGGCCGCTCTATCTGCTGGGTCCAAATC -3' | 12 |
| FGFP+ | 5'- CCCGAGCTCGAAGATTTTCTCGATAAGGAAG -3' | 13 |
| FGFP- | 5'- CCCGCGGCCGCATATAAAGCACTGTGCCACTAAG -3' | 14 |
| FGIP+ | 5'- CCCCCCGGGGAAGATTTTCTCGATAAGGAAG -3' | 15 |
| FGIP- | 5'- CCCTCTAGAATATAAAGCACTGTGCCACTAAG -3' | 16 |
| FGST1+ | 5'- CCCGAGCTCCGATTTCAAGGAGGACGG -3' | 17 |
| FGST1- | 5'- CCCGCGGCCGCCCATGCCATGTGTAATCCC -3' | 18 |
| RGFP+ | 5'- CCCCCCGGGCGATTTCAAGGAGGACGG -3' | 19 |
| RGFP- | 5'- CCCTCTAGACCATGCCATGTGTAATCCC -3' | 20 |
| RGIP+ | 5'- CCCGAGCTCGACCTTGGCAGACCTCAG -3' | 21 |
| RGIP- | 5'- CCCGCGGCCGCCCAGCTCGAACCACTTTT -3' | 22 |
| RGSL+ | 5'- CCCCCCGGGGACCTTGGCAGACCTCAG -3' | 23 |
| RGSL- | 5'- CCCTCTAGACCAGCTCGAACCACTTTT -3' | 24 |

2. Transformation of *Agrobacterium tumefaciens*

Freeze-thaw method is used to transform *agrobacterium tumefaciens*. A single colony LBA4404 or GV3101 (both purchased from Invitrogen company), 3 ml LB culture medium (containing 25 μg/ml rifamycin (Rif) and 50 μg/ml kanamycin (Kan) or gentamycin (Gen)), 28° C., 220 rpm, incubation overnight. 2 ml bacteria liquid, 50 ml LB culture medium (25 μg/ml Rif and 50 μg/ml Gen), 28° C., 220 rpm, cultured until $OD_{600}$=0.5 (about 6 h). Place the culture on ice for 30 min, 4° C., 5000 g centrifugation for 5 min. Re-suspend it in 10 ml 0.15 M NaCl. 4° C., 5000 g centrifugation for 5 min. Re-suspend it in 1 ml 20 mM $CaCl_2$, separate packed in 50 μl/tube, liquid nitrogen flash freezing, preserve competent cell at −70° C. Mix binary vectors containing target genes and 50 μl/tube competent cell, place it on ice for 30 min, liquid nitrogen flash freezing for 1 min. Thaw the bacterial liquid at 37° C. water bath for 5 min, add 1 ml LB culture medium, 28° C., 220 rpm, for 2-4 h culture. Take 50-100 μl LB culture medium painted plate (25 μl/ml Rif, 50 μg/ml Gen and 50 μg/ml Kanamycin (Kan) or hygromycin (Hyg)).

Example 5

Plant Transfection and Screening for Transgenic Progeny

In this embodiment, tobacco and *arabidopsis thaliana* are used as examples. Other plants may be transfected using similar methods.

a. Transgenes of Tobacco

Overnight culture *agrobacterium tumefaciens* LBA4404 containing target genes (28° C. overnight culture, until $OD_{600}$≈2.0). Cut aseptic tobacco leaf into roughly 0.1 $cm^2$ size, dip into *agrobacterium tumefaciens* culture medium for 5-10 min. Absorb extra *agrobacterium tumefaciens* culture medium with aseptic filter paper, place the dipped tobacco leaf onto ½ MS solid culture medium for 2 days without light. Then transfer the leaf to MS (containing 1 mg/L 6-BA) solid selection culture medium ($Kan^r$, $Cef^r$), change to fresh MS every 10-15 days, until bud grows from leaf wound, then transfer new buds into MS culture medium free of 6-BA, change to fresh MS after every 10-15 days, and transfer buds to soil after buds develop roots.

MS culture medium: 4.4 g/L Murashige and Skoog basal medium (Sigma, Cat. M5519), 15 g/L sucrose, 0.8% agar powder, 0.5 g/L MES, pH 5.7.

b. Transgenes of *Arabidopsis thaliana*

Floral dip method is used in the transfection of *arabidopsis thaliana* plant (Clough and Bent, 1998, Plant J. 16, 735-743). A single colony GV3101 containing binary vector, 3 ml LB culture medium (25 μg/ml Rif, 50 μg/ml Gen and 50 μg/ml Kan or Hyg), 28° C., 220 rpm, 12 h. 2 ml bacteria liquid, 50 ml LB culture medium (25 μg/ml Rif, 50 μg/ml Gen and 50 μg/ml Kan or Hyg), 28° C., 220 rpm, 12 h. 50 ml bacteria liquid, 250 ml LB culture medium (50 μg/ml Gen and 50 μg/ml Kan or Hyg), 28° C., 220 rpm, 12 h. 4200 rpm (2900 g), 15 min. Re-suspend the bacteria in a 500 ml 5% sucrose solution containing 0.02% Silwet L-77. Dip the floral part of plant in bacteria liquid for 5 seconds, place it flatly on a plastic basin, keep moisture, avoid light for 16-24 h, grow in greenhouse until blossom and producing seeds. Perform vernalization for T0 seeds at 4° C. for 2-4 d, treat with 20% bleaching water (Whitecat company, Shanghai) for 15 min, wash with sterile water for 3-4 times. Suspended in 0.5% Agarose (55° C.), placed onto LB culture medium of 0.6% agar (containing 50 μg/ml Kan or Hyg), 22° C., continuous illumination, for about 1 week, and transfer the green resistant plantlet to nutrient soil (turf:vermiculite:perlite=1:1:1) for growth.

c. Transgenes of Cotton

Cotton R15 (*Gossypium hirsutum* Linn) seeds are placed into MS0 culture medium after sterilization, germinate and grow in dark, 5-7 days later, cut aseptic seedling hypocotyls into about 1.0 cm segments as transformed explants. The explants are dipped and infected in *agrobacterium tumefaciens* bacteria liquid for 15-20 min, transferred onto co-culture medium MSB1, at 22° C. for 2 d without light. Transfer the explants onto culture medium MSB2 to induce callus. The explants regrow resistant test-tube plantlet after inducement of callus, propagation of callus and inducement of embryogenic callus (culture medium MSB3), body cell embryogenesis (culture medium MSB4). When regenerated plants develop 3-4 true leaves, engraft or transplant the plants and transfer the plants to garden pots in controlled climate rooms.

MS0: ½ MS salt+5 g/L glucose+7 g/L agar powder, pH 5.8.

MSB1: MS salt+B5 organic+30 g/L glucose+0.1 mg/L KT+0.1 mg/L 2,4-D+2.2 g/L Gelrite, pH 5.8.
MSB2: MSB1+500 mg/L cephalothin+80 mg/L kanamycin.
MSB3: MS salt+B5 organic+30 g/L glucose+2.5 g/L Gelrite, pH 5.8.
MSB4: MS salt+B5 organic+30 g/L glucose+1.0 g/L asparagus cochinchinensis amide+2.0 g/L glutamine+3.0 g/L Gelrite, pH 5.8; double $KNO_3$ in MS salt, remove $NH_4NO_3$.

Example 6

Molecular Biological Identification of Transgenic Plants

In this embodiment, select T3 generation homozygous strain of transgenic plants obtained from Example 5, after antibiotic selection, and identify the transgenic plants using Northern hybridization.
Use of Northern Blot Membrane Transfer for Detection of Interfering RNA:

Membrane transfer: extract RNA samples from transgenic plants using conventional methods, add 10× electrophoresis sample liquid into RNA samples, mix well, standing at 65° C. for 10 min, cool down on ice. Perform electrophoresis using 15% TBE-urea PAGE gel, 1×TBE electrophoresis buffer. Pre-electrophoresis 5-10 min and rinse sample wells with electrophoresis buffer prior to loading samples, remove urea extracted from wells. Load 10-20 µg total RNA into each well, with electric field intensity at 20 V/cm, stop electrophoresis when bromophenol blue dye migrates to the bottom of gel. Equilibrate the gel in 1×TBE for 10 min. Transfer RNA using Hofer Semi-Dry Transfer Units, Amersham, Cat. 80-6211-86. Transfer conditions: 40 mA (about 7-8 V), 2-4 h, Hybond-N⁺ (Amersham, Cat. RPN303B) nylon membrane. The nylon membrane is briefly washed with 6×SSC solution, ultraviolet crosslinking (120 mJ), sandwiched the membrane between two filter papers, baked at 80° C. for 1 h, ready for use.

Electrophoresis gel storage liquid: 15% polyacrylamide (30% Acyl/Bis, 19:1, Huashun, Cat. W443), 8 M urea, 1×TBE;
15% TBE-urea PAGE gel (10 mL): 10 mL electrophoresis gel storage liquid, 80 µL 10% ammonium persulphate, 5 µL TEMED, mix well.
10×TBE: 0.9M Tris, 0.9 M boric acid, 20 mM EDTA (pH 8.0) (Sigma, Cat. T4415);
10×electrophoresis sample liquid: (Ambion, cat. 8546G).

Probe labeling: use 25 ng purified PCR products as template labeling probes. Labeling probes is performed using Prime-a-Gene Labeling System (Promega, Cat. U1100). 37° C. warm bath for 1 h. Incubate the labeled probe in boiling water for 5 min, then immediately transferred on ice, ready for use.

Pre-hybridization and hybridization (using ExpressHyb system from Clontech): place the nylon membrane into a hybridization tube, wet with 6×SSC, ensure no air bubbles between membrane and tube wall. remove 6×SSC, add 5 mL hybridization liquid, perform pre-hybridization at 37° C. for 60 min. After pre-hybridization, replace with 5 mL fresh hybridization solution, add probes inside, mix well, and perform hybridization overnight.

Membrane washing and exposure to films: after hybridization, remove hybridization solution. At room temperature, wash membrane twice with 2×SSC, 0.05% SDS, 5 min each, then wash twice with 0.2×SSC, 0.1% SDS, 20 min each. Wrap the membrane with preservative film, stabilized with adhesive tape, with intensifying screen and X-ray film, −70° C., 2 days. The film is developed using D-72 liquid.

FIG. 4B shows the results of Northern blot analysis on GIP, GFP or GST1 sequence of dsRNA in transgenic tobacco and *arabidopsis thaliana*. In FIG. 4B, WT is wild-type plant control, lanes having signals show the expression of dsRNA of indicated genes in plants indicated.

Example 7

Effect on Cotton Bollworm by dsRNA Transgenic *Arabidopsis thaliana* and Tobacco Expressing GIP Gene Feed 3-day old cotton bollworm having the same growth vigor with dsGFP (control), dsGIP transgenic tobacco or *arabidopsis thaliana*, 4-7 days later, record weighs, dissect and harvest the mesenteron. Extract DNA and determine GIP expression using Northern blot analysis.
RNA Extraction:

Grind the materials (about 100 mg) in liquid nitrogen. Transfer it to a 1.5 ml centrifugal tube, add 1 mL Trizol (Invitrogen, Cat. 15596-018), mix well, stand at room temperature for 5 min. Centrifugate at 12,000 rpm for 10 min, discard precipitate. Add 200 µL trichloromethane into supernatant, mix well, centrifugate at 12,000 rpm for 10 min. Harvest the supernatant, add 500 µL isopropanol for RNA precipitation. Centrifugate at 12,000 rpm for 10 min, wash the precipitate with 70% ethanol, dry in vacuum, dissolve in 20-50 µL $H_2O$(RNase free).

Dilute RNA with 10 mM Tris-HCl (pH 7.5) to some extent, determine UV absorption values at wavelength of 200 nm-300 nm. RNA concentration=40 µg/mL×$A_{260}$×dilution ratio.
RNA Membrane Transfer for Common Northern Blot Analysis:

Add 5×RNA sample buffer and 10×RNA (formaldehyde) electrophoresis to RNA sample solution, mix well, stand at 65° C. for 10 min, cool down on ice. Load 15 µg total RNA into each line, 1.1% modified agarose gel is used in electrophoresis, 1×MOPS electrophoresis buffer, with electric field intensity of 8 V/cm. Stop the electrophoresis when bromophenol blue dye migrates to ⅔ of gel. Wash the gel with dd$H_2O$, and equilibrate the gel in 20×SSC for 40 min. Construct a transfer platform, 20×SSC used as transfer buffer, transfer RNA to Hybond-XL (Amersham, Cat. RPN303S) nylon membrane by capillary method (about 18 h). After transfer, mark the positions of sample wells on membrane with pencil, label the membrane by cutting out the upper left corner of the membrane. The membrane is briefly washed with 6×SSC solution, ultraviolet crosslinking (120 mJ), sandwitched the membrane between two filter papers, baked at 80° C. for 2 h, air-tight storage, ready for use.

The hybridization process is the same as Northern blot analysis of interfering RNA.

Figure 5:
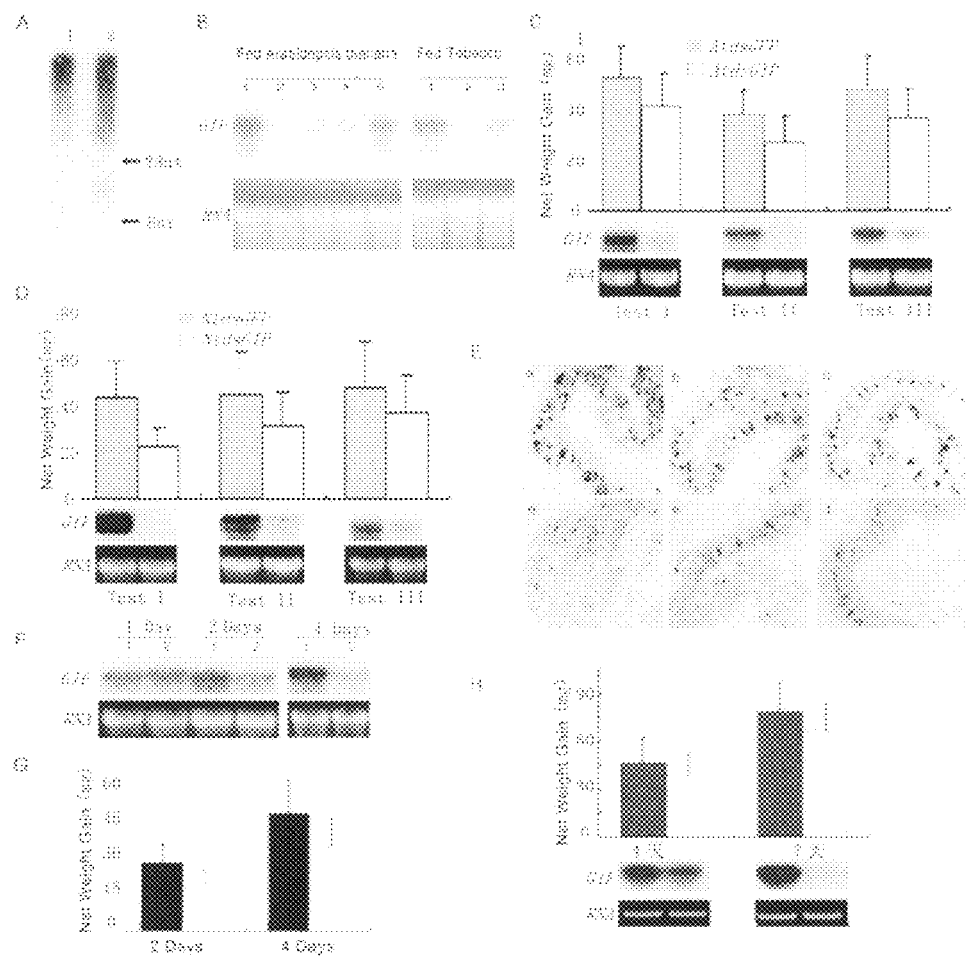
FIG. 5 shows the effects on cotton bollworm caused by the expression of dsRNA containing GIP sequence in transgenic *arabidopsis thaliana* and tobacco.

The results show that the GIP gene transcription is inhibited in the mesenteron of the cotton bollworm eating dsGIP *arabidopsis thaliana* AtdsGIP-3 (i.e. the third clone of transgenic *arabidopsis thaliana* expressing dsGIP detected in FIG. 4B of Example 6) or tobacco NtdsGIP-2 (i.e. the second clone of transgenic tobacco expressing dsGIP detected in FIG. 4B of Example 6) as compared to that of the cotton bollworm eating dsGFP *arabidopsis thaliana* AtdsGFP (i.e. the fifth clone of transgenic *arabidopsis thaliana* expressing dsGFP detected in FIG. 4B of Example 6) or tobacco NtdsGFP (i.e. the second clone of transgenic tobacco expressing dsGFP detected in FIG. 4B of Example 6) (control). The former cotton bollworm grow slowly. See FIG. 5 and FIG. 6 for details.

FIG. 5A shows Northern blot analysis on small RNA containing GIP sequence in the mesenteron of 3-day old cotton bollworm at 2 days after eating AtdsGIP-3 *arabidopsis thaliana*. Lane 1 and 2 are cotton bollworm eating AtdsGFP and AtdsGIP-3, respectively. A large amount of GIP small RNA molecules can be observed in the mesenteron of cotton bollworm after eating.

FIG. 5B shows Northern blot analysis on the changes on GIP gene transcription in the mesenteron of 3-day old cotton bollworm 4 days after eating different transgenic plants expressing dsRNA. In the results that show cotton bollworm eating *arabidopsis thaliana* expressing RNA of GIP gene (GIP in the figure), Lane 1, 2, 3, 4, and 5 represent GIP RNA test results of the mesenteron of cotton bollworm eating Atds GFP, and strain 2, 3, 4, and 5 of dsGIP transgenic *arabidopsis thaliana* in FIG. 4B, respectively, in the figure, RNA indicates control (i.e. 18s RNA). In the GIP test results of cotton bollworm eating tobacco, Lane 1, 2, and 3 represent GIP RNA test results of the mesenteron of cotton bollworm eating wild-type tobacco and NtdsGFP, and strain 2 of dsGIP transgenic tobacco detected in FIG. 4B. It can be seen that after eating plants containing dsGIP, the GIP gene transcription in the mesenteron of cotton bollworm is greatly reduced.

FIG. 5C shows the average body weight gain (upper) of 3-day old cotton bollworm 4 days after eating AtdsGFP, AtdsGIP-3, and changes in GIP gene transcription in the mesenteron detected by Northern blot analysis. Test I, II, and III represent three independent feeding tests. It can be seen that after eating AtdsGIP-3, the weight gain is obviously slower than those eating AtdsGFP. In addition, after eating AtdsGIP-3, the GIP gene transcription in the mesenteron of cotton bollworm is obviously lower than that eating AtdsGFP.

FIG. 5D shows the average body weight gain (upper) of 3-day old cotton bollworm 4 days after eating NtdsGFP, NtdsGIP-2, and changes in GIP gene transcription in the mesenteron detected by Northern blot analysis. Test I, II, and III represent three independent feeding tests. It can be seen that after eating NtdsGIP-2, the weight gain is obviously slower than those eating NtdsGFP. In addition, after eating NtdsGIP-2, the GIP gene transcription in the mesenteron of cotton bollworm is obviously lower than that eating NtdsGFP.

FIG. 5E show immunohistochemical analysis of GIP protein distribution in the mesenteron 4 days after eating NtdsGFP(a-c), NtdsGIP-2(d-f) tobacco, a, b, c or d, e, f represent individual test results. It can be seen that the GIP distribution in the mesenteron of cotton bollworm after eating dsGIP tobacco is relatively less.

FIG. 5F shows GIP gene transcription levels in the mesenteron of 3-day old cotton bollworm at day 1, 2, and 4 after eating NtdsGFP (1) and NtdsGIP-2 (2) tobacco. It can be seen that the transcription level of cotton bollworm eating NtdsGIP-2 is decreased over time; but the GIP gene transcription levels in the mesenteron of cotton bollworm eating NtdsGFP vary little.

FIG. 5G shows the average body weight gain of 3-day old cotton bollworm at day 2 and day 4 after eating NtdsGFP (black column) and NtdsGIP-2 (white column). It can be seen the weight gain of cotton bollworm eating NtdsGIP-2 is obviously lower than those eating NtdsGFP.

FIG. 5H shows the average body weight gain (upper) of 3-day old cotton bollworm at day 4 and day 5 after eating AtdsGFP (black column) and AtdsGIP-3 (white column) transgenic *Arabidopsis* and GIP gene transcription levels (down) detected by Northern blot analysis. It can be seen that the weight gain of cotton bollworm eating AtdsGIP-3 is obviously lower than those eating AtdsGFP. In addition, the GIP gene transcription levels in the mesenteron of cotton bollworm eating AtdsGIP-3 is obviously lower than those eating AtdsGFP.

Example 8

Effect on Cotton Bollworm by dsRNA Transgenic Cotton Expressing GIP Gene

Feed 3-day old cotton bollworm having the same growth vigor with R15 (control, *Gossypium hirsutum* Linn) and transgenic cotton ds-2, -7, -9, and -10 (4 highest expression strains in Northern blot analysis shown in FIG. 4B) for 4 days. Record weight. The results are shown in FIG. 6.

FIG. 6A shows the Northern blot analysis of dsGIP RNA in transgenic cotton. R15: *Gossypium hirsutum* Linn, 1-10: different transgenic cotton.

FIG. 6B shows the body weight gains of 3-day old cotton bollworm with the same growth vigor after eating R15 and different dsGIP transgenic cotton for 4 days. y-axis: net gain of body weight, in mg, by T-test, P<0.01.

It can be seen from the results in FIG. 6 that the growth is inhibited in cotton bollworm after eating dsRNA transgenic cotton expressing GIP gene.

Example 9

Effect on Cotton Bollworm by dsRNA Plant Expressing GST1 Gene

Feed 3-day old cotton bollworm with the same growth vigor dsGFP (control), dsGST1 transgenic *arabidopsis thaliana* for 4 days, record weigh, dissect and harvest the mesenteron. Divided into two parts, one for RNA extraction and Northern blot analysis for detecting GST1 expression, the other part for isolation of total protein for determining the enzymatic activity of GST.

Figure 7:
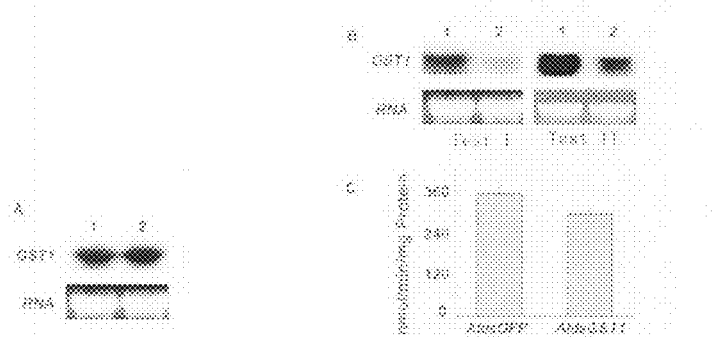
FIG. 7 shows the effect on cotton bollworm caused by the expression of dsRNA containing GST1 sequence in *arabidopsis thaliana*.

FIG. 7 shows the effect on cotton bollworm by transgenic *arabidopsis thaliana* dsGST1-5, which express GST1 gene dsRNA (i.e. strain 5 of dsGST 1 transgenic *arabidopsis thaliana* detected in FIG. 4B of Example 6).

FIG. 7A show the change in GST 1 gene expression in the mesenteron of 5-day old cotton bollworm with the same growth vigor 1 day after eating artificial diet containing 1 mg/g gossypol. Lane 1 and 2 are cotton bollworm eating artificial diet with or without 1 mg/g gossypol respectively. It can be seen that gossypol has no significant effect on the expression of GST1 gene in the mesenteron.

FIG. 7B shows the change in GST 1 gene expression in the mesenteron of 3-day old cotton bollworm with the same growth vigor 4 day after eating AtdsGFP (Lane 1) and dsGST1-5 (Lane 2) transgenic *arabidopsis thaliana*. Test I and II represent two independent feeding tests. It can be seen that the expression of GST 1 gene is interfered by corresponding interfering RNA of GST1. Thus, plant-mediated RNAi in insect is a common mechanism.

Protein Isolation:

Extraction of total proteins in the mesenteron of cotton bollworm: grind the mesenteron tissues in liquid nitrogen, add a proper amount of pre-cooled PBS, mix well, filter with 8-layer gauze, centrifugate (10,000 rpm, 10 min). Collect the supernatant, measure protein concentration using Bradford colorimetry, and analyze enzymatic activity.

Determine the Enzymatic Activity of GST

Measure the enzymatic activity according to glutathione-S transferase reagent kit provided by Nanjing Jiancheng Bioengineering Institute.

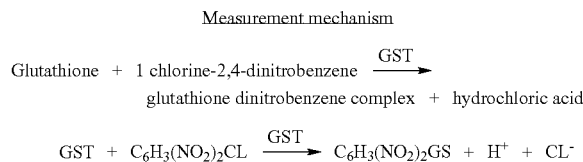

Measurement mechanism

GST can catalyze a reaction of reduced glutathione (GSH) and 1 chlorine-2,4-dinitrobenzene (CDNB substrate), within a certain reaction time, the enzymatic activity has a linear relationship with the changes in substrate concentration before and after the reaction.

FIG. 7C shows the results of GST enzymatic activity. It can be seen that after eating dsGST1 transgenic *arabidopsis thaliana*, the enzymatic activity of GST in the gut of cotton bollworm is significantly reduced.

Example 10

Large Fragment dsRNA can Also Effectively Silence Target Genes

According to Example 5, which provides methods for generating transgenic *arabidopsis thaliana* and for screening transgenic progeny, transfect dsGIP into dcl2, dcl3, dcl4 triple mutant *arabidopsis thaliana* plant (dcl2, dcl3, dcl4 triple mutant obtained from Z Xie, Center for Gene Research and Biotechnology, Department of Botany and Plant Pathology, Oregon State University, Corvallis, Oreg. 97331, USA) to obtain the transgenic *arabidopsis thaliana*. Select 4 transgenic strains, dcl AtdsGIP-11 to dcl AtdsGIP-14 (dcl 11-14 for short in FIG. 8), as control, select two transgenic strains in Example 6, AtdsGIP-7 and AtdsGIP-8 (WT 7-8 for short in FIG. 8) as control. Extract RNA according to the method described in Example 7 for Northern blot analysis. Take 3-day old cotton bollworm with the same growth vigor, feed dcl AtdsGIP (11-14) and AtdsGIP (7, 8) (as control) for 3 days, then dissect and harvest the mid gut. Extract RNA and perform Northern blot analysis for GIP expression. The results are shown in FIG. 8. FIG. 8a shows large fragment dsGIP in transgenic *arabidopsis thaliana* detected by Northern blot analysis. FIG. 8b shows small molecule dsGIP in transgenic *arabidopsis thaliana* detected by Northern blot analysis. FIG. 8c shows the GIP transcript in the mesenteron of 3-day old cotton bollworm larva 3 days after eating different transgenic plants. RNA hybridization signal is quantified by Fuji phosphor screen, ACT used as internal control, to calculate relative amount (GIP/ACT). The relative amount of GIP in the mesenteron of cotton bollworm eating non-transgenic plants is defined as 1. WT: wild-type *arabidopsis thaliana* (Col0) background, dcl: dcl2 dcl3 dcl4 triple mutant background. CK: non-transgenic plant, 7-14 represent different transgenic plants.

The results of FIG. 8 are shown in dcl2 dcl3 dcl4 triple mutant background, large fragment dsRNA, as compared to wild-type transgenic plants, has significantly accumulated. A great amount of large fragment dsRNA is detected in AtdsGIP-13 transgenic plant, but a very low amount of small molecule dsRNA is detected. If cotton bollworm eats this transgenic plant, the GIP gene transcription in the mesenteron is significantly inhibited and highly effective. It shows that during plant-mediated insect gene RNA interference, the large fragment dsRNA generated in plant body also participate in this process, and is more effective.

All the literatures mentioned herein are incorporated by reference in this invention, like each literature reference is solely cited. And it should be appreciated that the ordinary skilled persons in the art can modify or change the invention after reading the above description of the invention, these variations also fall within the scope of the claims of the invention.

The invention claimed is:

1. A method for improving insect resistance of a plant, comprising the following steps:
   transfecting a construct for expressing an insect gene dsRNA into a plant cell, a tissue or an organ, wherein said construct for expressing the insect gene dsRNA is double-stranded, and its sense strand or antisense strand contains a structure as shown in Formula 1:

$Seq_{sense}$-X-$Seq_{antisense}$    Formula 1 wherein,
   $Seq_{sense}$ is a sense sequence or a fragment of an insect gene, wherein said sense sequence and said fragment are at least 50 bp long;
   $Seq_{antisense}$ is a sequence or a fragment fully complementary to $Seq_{sense}$, wherein said sequence and said fragment are at least 50 bp long;
   X is an intervening sequence between $Seq_{sense}$ and $Seq_{antisense}$, and said intervening sequence is complementary to neither $Seq_{sense}$ nor $Seq_{antisense}$,
   wherein the insect is a Lepidoptera insect, and wherein the insect gene dsRNA can inhibit growth or development of the insect after feeding to the insect, and wherein the insect gene encodes GIP having the amino acid sequence of SEQ ID NO: 2.

2. The method of claim 1, wherein said construct is on an expression vector, and said expression vector comprises a promoter for activating gene transcription in the plant.

3. The method of claim 1, wherein insect gene is expressed in stomach or intestines of an insect.

4. The method of claim 1, wherein said plant is selected from dicotyledon, monocotyledon or gymnosperm.

5. The method of claim 1, wherein said insect is selected from those that eat plants.

6. The method of claim 1, wherein said intervening sequences is 80-300 bp long.

7. The method of claim 1, wherein after the construct for expressing the insect gene dsRNA is transfected into the plant cell, the tissue or the organ, the insect gene dsRNA of Formula II is formed in the plant cell, the tissue or the organ,

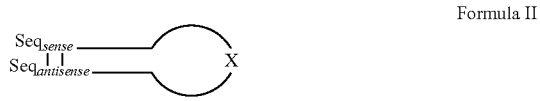

Formula II wherein,
$Seq_{sense}$, $Seq_{antisense}$ and X are as defined in claim 1,
|| indicates hydrogen bonds formed between $Seq_{sense}$ and $Seq_{antisense}$.

8. The method of claim 1, wherein the insect gene comprises the nucleotide sequence of SEQ ID NO: 1.

9. A transgenic plant or plant cell comprising the construct used in the method of claim 1.

10. The transgenic plant or plant cell of claim 9, wherein the insect gene is GIP having the nucleotide sequence of SEQ ID NO: 1.

* * * * *

SEQUENCE LISTING

```
<160> NUMBER OF SEQ ID NOS: 24

<210> SEQ ID NO 1
<211> LENGTH: 1904
<212> TYPE: DNA
<213> ORGANISM: Helicovepa armigera

<400> SEQUENCE: 1
ggcacgaggc gaagcttcac catgatcact tcattgctac taacggcagt ttttgtgata      60
atcttcacaa tctacctcgt gtccaagaaa aagtaccaat actgggagaa aaggaaagta     120
ccacatttac ctccggttcc tctcctggga aattttggga actttatcct gcagaggcaa     180
tttcttggct acacattaca acaaatatgt ggaaagtttc ccaacgtacc atacgtgggt     240
gcctattttg gcacagaacc tgccctgatc gtccaagatc ctgaacacat caagctcgtc     300
atgactaagg acttctactt cttcagttcc cgtgagatat ctgaatatgc cgacagggaa     360
aggtttactc agaacctctt ctccacttcc ggaaacaaat ggaaggtgtt acgtcagaac     420
ctgactccag tgtttacctc cgcgaagatg aagaacatgt tccatttgat cgaaaagtgt     480
tctcacgtgt tcgaagattt tctcgataag gaagccaaaa gcaacgaggt cgaaatgagg     540
gctcttgtag cgagatacac tatggactgc ataggaacct gtgcatttgg cgttgaaaca     600
```

```
aaaaccatga atgtgacgga aaataatccg tttacagcag taggtaacag catttcatg      660 ttaagccggg tccaaggatt taaatttgtt ttgagaggta tctacccttc acttttctac     720
ttgttgggat tcagaactct tccaccagaa gttaatgcat tcttctccaa tttaatgact    780
ggagttttta agggacgcaa ctatacgccc acatctcgga atgactttgt cgatttcgta    840
ttgaagtgga aacaaaataa aactatgaca ggggacagtc tgactaacat gaaatatgat    900
tcacagaaaa aagtgacttt agaagtcgac gatgatctct tagtggcaca gtgctttata   960
ttttttgctg ctggatatga aacttcggcc accactttga gttttacttt gtatgagttg   1020
gcgaaacacc cagaagctca gaagagagct atagccgagg tggacgatta tctgcggcga   1080
cacaacaatg agctgaagta cgagtgcctt tcggagatgc catttgtaga agcgtgcttt   1140
gatgagactc ttcgtaaata tccagtttta agtttgttaa ctcgcgaagt ggtagaggat   1200
tacactttcc cttcgggatt gaaggtagag aaaggtctcc gtatattcct gcctctgtat   1260
cacttgcacc ataacccgga gttcttcccg gatccggagg agtataggcc tgagcggttc   1320
ctgcctgaga acaaggataa aataaagccg tacacgtaca tgcccttcgg tgaaggcccg   1380
agactttgta ttggaatgag attcgcgaaa atgcaaatga ccgctggaat aataactttg   1440
ctgaaaaaat accgtttgga actggctcca gggatgcccc agaatattga atttgaacct   1500
aattcttttg tctcgcaagt tgcgggagga atcaatctga agatgataaa agagaaagt    1560 tgggaaggaa gactactgaa gaacctcgaa aaggcatatt aaaaaatttg acgttcagtt   1620
atataatctt gtatgactaa tcataattac gctttatgtc tggactatca tcacgtagca   1680
cttatcacgc gatagcaaat tataaatagc aaatgttgtg attgattaca tgattgattt   1740
ttttttaaat taatatttag attgattagc ttttaaaaat tgtgtcaaat atgttaaatt   1800
tgaaatgtcg ttataagttg acagtaaagt agcagtaaaa gttttttttt ttagcgcatt   1860
taaataaaag cttgttttta aagattaaaa aaaaaaaaa aaaa                     1904
```

<210> SEQ ID NO 2
<211> LENGTH: 526
<212> TYPE: PRT
<213> ORGANISM: Helicovepa armigera

<400> SEQUENCE: 2

```
Met Ile Thr Ser Leu Leu Leu Thr Ala Val Phe Val Ile Ile Phe Thr
1               5                   10                  15

Ile Tyr Leu Val Ser Lys Lys Tyr Gln Tyr Trp Glu Lys Arg Lys
            20                  25                  30

Val Pro His Leu Pro Pro Val Pro Leu Leu Gly Asn Phe Gly Asn Phe
        35                  40                  45

Ile Leu Gln Arg Gln Phe Leu Gly Tyr Thr Leu Gln Gln Ile Cys Gly
    50                  55                  60

Lys Phe Pro Asn Val Pro Tyr Val Gly Ala Tyr Phe Gly Thr Glu Pro
65                  70                  75                  80

Ala Leu Ile Val Gln Asp Pro Glu His Ile Lys Leu Val Met Thr Lys
                85                  90                  95

Asp Phe Tyr Phe Phe Ser Ser Arg Glu Ile Ser Glu Tyr Ala Asp Arg
            100                 105                 110

Glu Arg Phe Thr Gln Asn Leu Phe Ser Thr Ser Gly Asn Lys Trp Lys
        115                 120                 125

Val Leu Arg Gln Asn Leu Thr Pro Val Phe Thr Ser Ala Lys Met Lys
    130                 135                 140
```

Asn Met Phe His Leu Ile Glu Lys Cys Ser His Val Phe Glu Asp Phe
145                 150                 155                 160

Leu Asp Lys Glu Ala Lys Ser Asn Glu Val Glu Met Arg Ala Leu Val
            165                 170                 175

Ala Arg Tyr Thr Met Asp Cys Ile Gly Thr Cys Ala Phe Gly Val Glu
            180                 185                 190

Thr Lys Thr Met Asn Val Thr Glu Asn Asn Pro Phe Thr Ala Val Gly
            195                 200                 205

Asn Ser Ile Phe Met Leu Ser Arg Val Gln Gly Phe Lys Phe Val Leu
    210                 215                 220

Arg Gly Ile Tyr Pro Ser Leu Phe Tyr Leu Leu Gly Phe Arg Thr Leu
225                 230                 235                 240

Pro Pro Glu Val Asn Ala Phe Phe Ser Asn Leu Met Thr Gly Val Phe
                245                 250                 255

Lys Gly Arg Asn Tyr Thr Pro Thr Ser Arg Asn Asp Phe Val Asp Phe
                260                 265                 270

Val Leu Lys Trp Lys Gln Asn Lys Thr Met Thr Gly Asp Ser Leu Thr
            275                 280                 285

Asn Met Lys Tyr Asp Ser Gln Lys Lys Val Thr Leu Glu Val Asp Asp
290                 295                 300

Asp Leu Leu Val Ala Gln Cys Phe Ile Phe Phe Ala Ala Gly Tyr Glu
305                 310                 315                 320

Thr Ser Ala Thr Thr Leu Ser Phe Thr Leu Tyr Glu Leu Ala Lys His
                325                 330                 335

Pro Glu Ala Gln Lys Arg Ala Ile Ala Glu Val Asp Asp Tyr Leu Arg
                340                 345                 350

Arg His Asn Asn Glu Leu Lys Tyr Glu Cys Leu Ser Glu Met Pro Phe
            355                 360                 365

Val Glu Ala Cys Phe Asp Glu Thr Leu Arg Lys Tyr Pro Val Leu Ser
            370                 375                 380

Leu Leu Thr Arg Glu Val Val Glu Asp Tyr Thr Phe Pro Ser Gly Leu
385                 390                 395                 400

Lys Val Glu Lys Gly Leu Arg Ile Phe Leu Pro Leu Tyr His Leu His
                405                 410                 415

His Asn Pro Glu Phe Phe Pro Asp Pro Glu Glu Tyr Arg Pro Glu Arg
                420                 425                 430

Phe Leu Pro Glu Asn Lys Asp Lys Ile Lys Pro Tyr Thr Tyr Met Pro
            435                 440                 445

Phe Gly Glu Gly Pro Arg Leu Cys Ile Gly Met Arg Phe Ala Lys Met
            450                 455                 460

Gln Met Thr Ala Gly Ile Ile Thr Leu Leu Lys Lys Tyr Arg Leu Glu
465                 470                 475                 480

Leu Ala Pro Gly Met Pro Gln Asn Ile Glu Phe Glu Pro Asn Ser Phe
                485                 490                 495

Val Ser Gln Val Ala Gly Gly Ile Asn Leu Lys Met Ile Lys Arg Glu
            500                 505                 510

Ser Trp Glu Gly Arg Leu Leu Lys Asn Leu Glu Lys Ala Tyr
            515                 520                 525

<210> SEQ ID NO 3
<211> LENGTH: 840
<212> TYPE: DNA
<213> ORGANISM: Helicovepa armigera

<400> SEQUENCE: 3

```
ggcacgaagg gcgaatcaca gtgtgagata gaacaattca gaatgtcctt agacttgtat    60
tacgcccctg ggtcggcacc gtgccgagtg gtcctgctcg tagcagcagc cctcgacgtc   120
cattttaatc cccacatctt aaacttaaga aatggcgaac acctcacacc agaattttg    180 aagctgaatc cccaacacac agtgcccaca ctagtcgacg gcgacttctc tctatgggag   240
tcgagagcca tcggcaaata cttggtgaac aaatatggcg gcgagaacaa cgacttgtat   300
cctagtgatc ctaaagccag ggcgatcgtc gaccagagac tagacttcga cttgggaacg   360
ctttacccaa gatttggaaa ctacatctat cctcaaatct tcggtggagc gaaagcagat   420
gaggctctgc tcaagaagct ggaggaagct ctgcacttcc tcaacacatt cctcgaaggt   480
cagaagtacg ctgcgggtga caaactgacc ttggcagacc tcagtctcgt ggcgactgtg   540
tccactatag acgccgtcga catcagcctg aaggaatatc ccaatgttga aaagtggttc   600
gagctggtga aagcgactgc cccgggatac caggaagcaa atgaagctgg ccttaaagca   660
ttcagagcta tggtagcgca gttaaaagct aaaactgaat tgtaagtgta gcagcataat   720
gcaatattgt atttagaggt acagaagtaa gagagcattt gctcgcagta ataatagtaat   780 actcgcattt tgtaagaaat tgtcgttaag taaaaatatt tatatttgaa aaaaaaaaa    840
```

<210> SEQ ID NO 4
<211> LENGTH: 220
<212> TYPE: PRT
<213> ORGANISM: Helicovepa armigera

<400> SEQUENCE: 4

```
Met Ser Leu Asp Leu Tyr Tyr Ala Pro Gly Ser Ala Pro Cys Arg Val
1               5                   10                  15

Val Leu Leu Val Ala Ala Ala Leu Asp Val His Phe Asn Pro His Ile
            20                  25                  30

Leu Asn Leu Arg Asn Gly Glu His Leu Thr Pro Glu Phe Leu Lys Leu
        35                  40                  45

Asn Pro Gln His Thr Val Pro Thr Leu Val Asp Gly Asp Phe Ser Leu
    50                  55                  60

Trp Glu Ser Arg Ala Ile Gly Lys Tyr Leu Val Asn Lys Tyr Gly Gly
65                  70                  75                  80

Glu Asn Asn Asp Leu Tyr Pro Ser Asp Pro Lys Ala Arg Ala Ile Val
                85                  90                  95

Asp Gln Arg Leu Asp Phe Asp Leu Gly Thr Leu Tyr Pro Arg Phe Gly
            100                 105                 110

Asn Tyr Ile Tyr Pro Gln Ile Phe Gly Gly Ala Lys Ala Asp Glu Ala
        115                 120                 125

Leu Leu Lys Lys Leu Glu Glu Ala Leu His Phe Leu Asn Thr Phe Leu
    130                 135                 140

Glu Gly Gln Lys Tyr Ala Ala Gly Asp Lys Leu Thr Leu Ala Asp Leu
145                 150                 155                 160

Ser Leu Val Ala Thr Val Ser Thr Ile Asp Ala Val Asp Ile Ser Leu
                165                 170                 175

Lys Glu Tyr Pro Asn Val Glu Lys Trp Phe Glu Leu Val Lys Ala Thr
            180                 185                 190

Ala Pro Gly Tyr Gln Glu Ala Asn Glu Ala Gly Leu Lys Ala Phe Arg
        195                 200                 205

Ala Met Val Ala Gln Leu Lys Ala Lys Thr Glu Leu
    210                 215                 220
```

```
<210> SEQ ID NO 5
<211> LENGTH: 21
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 5
gtgctttgat gagactcttc g                                              21

<210> SEQ ID NO 6
<211> LENGTH: 23
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 6
tacatttgct atttataatt tgc                                            23

<210> SEQ ID NO 7
<211> LENGTH: 22
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 7
gaagattttc tcgataagga ag                                             22

<210> SEQ ID NO 8
<211> LENGTH: 23
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 8
atataaagca ctgtgccact aag                                            23

<210> SEQ ID NO 9
<211> LENGTH: 18
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 9
gaccttggca gacctcag                                                  18

<210> SEQ ID NO 10
<211> LENGTH: 18
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 10
ccagctcgaa ccactttt                                                  18
```

```
<210> SEQ ID NO 11
<211> LENGTH: 32
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 11
ccctctagaa cgttgtaagt ctgattttttg ac                             32

<210> SEQ ID NO 12
<211> LENGTH: 32
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 12
cccgcggccg ctctatctgc tgggtccaaa tc                              32

<210> SEQ ID NO 13
<211> LENGTH: 31
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 13
cccgagctcg aagatttttct cgataaggaa g                              31

<210> SEQ ID NO 14
<211> LENGTH: 34
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 14
cccgcggccg catataaagc actgtgccac taag                            34

<210> SEQ ID NO 15
<211> LENGTH: 31
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 15
ccccccgggg aagatttttct cgataaggaa g                              31

<210> SEQ ID NO 16
<211> LENGTH: 32
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 16
ccctctagaa tataaagcac tgtgccacta ag                              32

<210> SEQ ID NO 17
```

<211> LENGTH: 27
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 17
cccgagctcc gatttcaagg aggacgg 27

<210> SEQ ID NO 18
<211> LENGTH: 30
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 18
cccgcggccg cccatgccat gtgtaatccc 30

<210> SEQ ID NO 19
<211> LENGTH: 27
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 19 cccccccgggc gatttcaagg aggacgg 27

<210> SEQ ID NO 20
<211> LENGTH: 28
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 20
ccctctagac catgccatgt gtaatccc 28

<210> SEQ ID NO 21
<211> LENGTH: 27
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 21
cccgagctcg accttggcag acctcag 27

<210> SEQ ID NO 22
<211> LENGTH: 29
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 22
cccgcggccg cccagctcga accactttt 29

<210> SEQ ID NO 23
<211> LENGTH: 27

```
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 23 cccccgggg accttggcag acctcag                                               27

<210> SEQ ID NO 24
<211> LENGTH: 27
<212> TYPE: DNA
<213> ORGANISM: Artifical Sequence
<220> FEATURE:
<221> NAME/KEY: misc_feature
<223> OTHER INFORMATION: Synthetic Sequecne

<400> SEQUENCE: 24
ccctctagac cagctcgaac cactttt                                              27
```